US00RE36974E

United States Patent [19]

Bonutti

[11] E Patent Number: Re. 36,974

[45] Reissued Date of Patent: Nov. 28, 2000

[54] SUTURE ANCHOR

[76] Inventor: Peter M. Bonutti, 1303 W. Evergreen Plz., Effingham, Ill. 62401

[21] Appl. No.: 09/033,020

[22] Filed: Mar. 2, 1998

Related U.S. Patent Documents

Reissue of:

[64] Patent No.: 5,496,348
Issued: Mar. 5, 1996
Appl. No.: 08/445,049
Filed: May 19, 1995

U.S. Applications:

[62] Division of application No. 08/344,466, Nov. 23, 1994, Pat. No. 5,527,343, which is a division of application No. 08/062,295, May 14, 1993, Pat. No. 5,403,348.

[51] Int. Cl.[7] ..... A61B 17/00

[52] U.S. Cl. ..... 606/232; 606/72

[58] Field of Search ..... 606/232, 72–74, 606/104, 139

[56] References Cited

U.S. PATENT DOCUMENTS

| | | | |
|---|---|---|---|
| 2,199,025 | 4/1940 | Conn . | |
| 3,625,220 | 12/1971 | Engelsher . | |
| 3,648,705 | 3/1972 | Lary . | |
| 4,210,148 | 7/1980 | Stivala . | |
| 4,235,238 | 11/1980 | Oglu et al. . | |
| 4,395,798 | 8/1983 | McVey . | |
| 4,409,974 | 10/1983 | Freedland . | |
| 4,448,194 | 5/1984 | DiGiovanni et al. . | |
| 4,669,473 | 6/1987 | Richards et al. . | |
| 4,741,330 | 5/1988 | Hayhurst . | |
| 4,750,492 | 6/1988 | Jacobs . | |
| 4,823,794 | 4/1989 | Pierce . | |
| 4,898,156 | 2/1990 | Gatturna et al. . | |
| 4,968,315 | 11/1990 | Gatturna . | |
| 5,009,663 | 4/1991 | Broome . | |
| 5,037,422 | 8/1991 | Hayhurst et al. . | |
| 5,041,129 | 8/1991 | Hayhurst et al. . | |
| 5,046,513 | 9/1991 | Gatturna et al. . | |
| 5,053,047 | 10/1991 | Yoon . | |
| 5,100,417 | 3/1992 | Cerier et al. . | |
| 5,102,421 | 4/1992 | Anspach, Jr. . | |
| 5,123,914 | 6/1992 | Cope . | |
| 5,141,520 | 8/1992 | Goble et al. . | |
| 5,156,616 | 10/1992 | Meadows et al. . | |
| 5,176,682 | 1/1993 | Chow . | |
| 5,180,388 | 1/1993 | DiCarlo . | |
| 5,203,784 | 4/1993 | Ross et al. . | |
| 5,203,787 | 4/1993 | Noblitt et al. . | |
| 5,258,016 | 11/1993 | DiPoto et al. . | |
| 5,366,480 | 11/1994 | Corrivean et al. | 606/232 |
| 5,464,427 | 11/1995 | Curtis et al. | 606/232 |

FOREIGN PATENT DOCUMENTS 1903016 of 1970 Germany .

*Primary Examiner*—Michael Buiz
*Assistant Examiner*—Vikki Trinh
*Attorney, Agent, or Firm*—Tarolli, Sundheim, Covell, Tummino & Szabo L.L.P.

[57] ABSTRACT

The present invention is an anchor for securing a suture in the body. The anchor includes a tubular wall having a central axis. The tubular wall has a proximal end and a distal end each free of axially inwardly extending slots. The tubular wall has an inner surface extending for the entire length of the tube and defining in the anchor a central opening extending between the proximal end and the distal end. The anchor has a width less than its length. A suture may extend through the anchor within the central opening. First and second end portions of the suture extend out of opposite ends of the anchor and are sufficiently long to project out of the body when the suture is secured in the body by the anchor. The anchor has an anchoring orientation in the body achieved by manipulation of the distal end of the anchor by pulling on the second end portion of the suture. The anchor has a removal orientation in the body achieved by manipulation of the proximal end of the anchor by pulling on the first end portion of the suture. The present invention also relates to a method of anchoring to a bone a suture having first and second end portions.

6 Claims, 7 Drawing Sheets

SUTURE ANCHOR

Matter enclosed in heavy brackets [ ] appears in the original patent but forms no part of this reissue specification; matter printed in italics indicates the additions made by reissue.

This application is a *reissue of U.S. patent application Ser. No. 08/445,049, now U.S. Pat. No. 5,496,348, which is a* divisional of U.S. patent application Ser. No. 08/344,466, filed on Nov. 23, 1994 [pending] *now U.S. Pat. No. 5,527, 343*. The aforementioned application Ser. No. 08/344,466 is itself a divisional of U.S. application Ser. No. 08/062,295, filed May 14, 1993 (now U.S. Pat. No. 5,403,348). The benefit of the earlier filing dates of the aforementioned applications Ser. Nos. 08/344,466 and 08/062,295 is hereby claimed.

BACKGROUND OF THE INVENTION

1. Technical Field

The present invention relates to the arts of medicine and surgery, and more particularly relates to apparatus and method for securing a suture in body tissue.

2. Description of the Prior Art

Suture anchors have been developed for anchoring sutures during open surgery and arthroscopic surgery with single side access. With a suture anchored in tissue, it is possible to apply force to the suture to hold other body tissue or implanted devices.

It is desirable that a suture anchor be as small as possible in order to minimize damage to the tissue in which the suture is anchored. It is also desirable that a suture anchor be easily attached, hold the suture firmly in place, and be easily removable without trauma. Most current suture anchors, especially those for anchoring in bone, are not easily removable.

SUMMARY OF THE INVENTION

The present invention is an anchor for securing a suture in the body. The suture anchors of the present invention are usable in soft tissue as well as in bone. The anchor includes a tubular wall having a central axis. The tubular wall has a proximal end and a distal end each free of axially inwardly extending slots. The tubular wall has an inner surface extending for the entire length of the tube and defining in the anchor a central opening extending between the proximal end and the distal end. The anchor has a width less than its length.

A suture may extend through the anchor within the central opening. First and second end portions of the suture extend out of opposite ends of the anchor and are sufficiently long to project out of the body when the suture is secured in the body by the anchor.

The anchor has an anchoring orientation in the body achieved by manipulation of the distal end of the anchor by pulling on the second end portion of the suture. The anchor has a removal orientation in the body achieved by manipulation of the proximal end of the anchor by pulling on the first end portion of the suture.

The present invention also relates to a method of anchoring to a bone a suture having first and second end portions. The method includes the steps of:

threading the suture through an anchor having proximal and distal end portions so that the suture extends completely through the anchor, the first end portion of the suture extends in a first direction out of the proximal end portion of the anchor, and the second end portion of the suture extends in a second direction out of the distal end portion of the anchor;

inserting the suture and the anchor distally into the bone in an insertion/release orientation in which (a) the first end portion of the suture extends proximally from the proximal end portion of the anchor to a location outside of the bone, and (b) the second end portion of the suture extends distally into the bone from the second end portion of the anchor and wraps proximally back around the anchor and extends proximally past the outside of the anchor to the location outside of the bone, the anchor and the first and second end portions of the suture being generally parallel with each other when the anchor and the suture are in the insertion/release orientation; and causing the anchor to pivot within the bone to an anchoring orientation different from the insertion/release orientation by pulling at the location outside of the bone on the second end portion of the suture.

The invention also relates to a method of anchoring a suture to a bone having a harder outer layer and a softer inner layer. The method includes the steps of: providing an opening extending from a location outside of the bone through the harder outer layer of bone into the softer inner layer of bone; connecting a suture with a suture anchor; inserting the suture anchor with the suture connected thereto through the opening into the softer inner layer of bone; and pulling on the suture to change the orientation of the anchor within the softer inner layer of bone to block movement of the anchor out of the opening.

The invention also relates to a method of anchoring a suture in soft tissue.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DESCRIPTION OF PREFERRED EMBODIMENT

Figure 1:
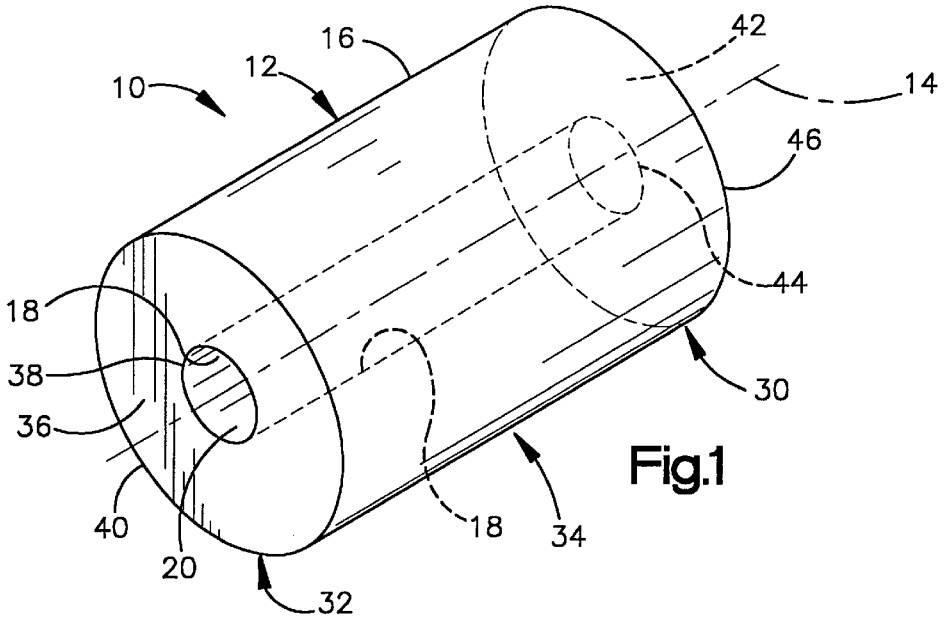
FIG. 1 is a perspective view of a suture anchor in accordance with the present invention.

The present invention relates to a suture anchor and particularly to an anchor for anchoring a suture to body tissue such as bone and to a method for such anchoring and removal. The present invention is applicable to various anchor constructions. As representative of the present invention, FIG. 1 illustrates a suture anchor 10. The anchor 10 is a cylindrical member with a tubular wall 12 extending about a longitudinal axis 14 of the anchor. The wall 12 has a cylindrical outer surface 16 and a cylindrical inner surface 18. The inner surface 18 of the anchor 10 defines a cylindrical central channel 20 extending longitudinally through the anchor 10.

The anchor 10 has a first end portion indicated generally at 30, a second end portion indicated at 32, and an intermediate portion indicated generally at 34. The present description assumes that the first end portion 30 will be inserted into the body tissue as the leading end portion of the anchor 10. For purposes of the present description, the anchor first end portion 30 will therefore be described as a distal end portion of the anchor, and the second end portion 32 will be described as a proximal end portion. The anchor 10 as illustrated in FIG. 1 is uniform and symmetrical in its construction, and accordingly either end of the anchor 10 can serve as the leading or distal end portion of the anchor upon insertion.

The anchor proximal end portion 32 has an annular end face 36 extending radially between an inner periphery 38 and an outer periphery 40. The inner periphery 38 is the proximal end of the cylindrical inner surface 18 and of the central channel 20 of the anchor 10. The distal end portion 30 of the anchor 10 includes an annular end face 42 extending radially between an inner periphery 44 and an outer periphery 46. The inner periphery 44 terminates the distal end of the cylindrical inner surface 18 and of the central channel 20 of the anchor 10.

The anchor 10 is made of a biocompatible material. Suitable materials include stainless steel or titanium (presently preferred), cobalt chrome and other biocompatible metals. Plastic can also by used, suitable materials including polyethylene; and biodegradable materials such as PLA and PGA when the anchor is to be left in the body.

The anchor 10 is longer than it is wide. That is, the length of the anchor 10, between its distal end face 42 and its proximal end face 36, is greater than the outer diameter of the anchor 10. The anchor 10 must be long enough, relative to its width, so that when rotated it does not accidentally back out of an opening through which it is inserted into body tissue such as bone. More specifically, the anchor must be longer than the diameter of the opening through which it is inserted into body tissue such as bone. However, the anchor 10 should not be longer than necessary, so as to avoid unnecessary tissue damage.

Applicants have found that a suitable range of dimensions is from about length equals 1.5 times width to about length equals four times width. It is preferred that the length to width ratio be about three to two for an anchor in bone, and longer (possibly four to one) for a soft tissue anchor. One anchor that has been constructed is about two millimeters long, about one millimeter in diameter, and has a central channel with a diameter of about one-half millimeter. This central channel diameter is suitable for receiving a number two suture therethrough. Other anchors which have been constructed and tested range in length from three millimeters to four millimeters.

The anchor 10 is for use in anchoring a suture such as a suture 50 (FIG. 4) in body tissue such as bone. The suture 50 is threaded completely through the central channel 20 of the anchor 10. A distal portion 52 of the suture 50, including a suture distal end 54, extends from the distal end portion 30 of the anchor 10. A proximal portion 56 of the suture 50, including a suture proximal end 58, extends from the proximal end portion 32 of the anchor 10. An intermediate portion 60 of the suture 50 is disposed within the anchor central channel 20, inside the wall 12 of the anchor 10.

The inner diameter of the anchor 10, i.e., the cross sectional width of the central channel 20 as defined by the anchor inner surface 18, is preferably greater than the width or diameter of the suture 50. Thus, the suture 50 can pass freely through the anchor 10. The anchor inner surface 18 guides movement of the suture 50 within the anchor 10. There are no knots holding the suture to the anchor 10. Knots tend to weaken the system. Also, there are no axially extending slots in the anchor 10 into which the suture 50 can enter.

When the suture 50 extends through the anchor 10, the suture is engageable with the proximal and distal end portions 32 and 30, respectively, of the anchor. The anchor proximal end portion 32, including the end face 36 and the inner edge 38, directs movement of the suture 50 into and out of the anchor 10 through the proximal end portion 32. The anchor distal end portion 30, including the annular end face 42 with its edges 44 and 46, directs movement of the suture 50 into and relative to the distal end portion 30 of the anchor 10.

Figure 5:
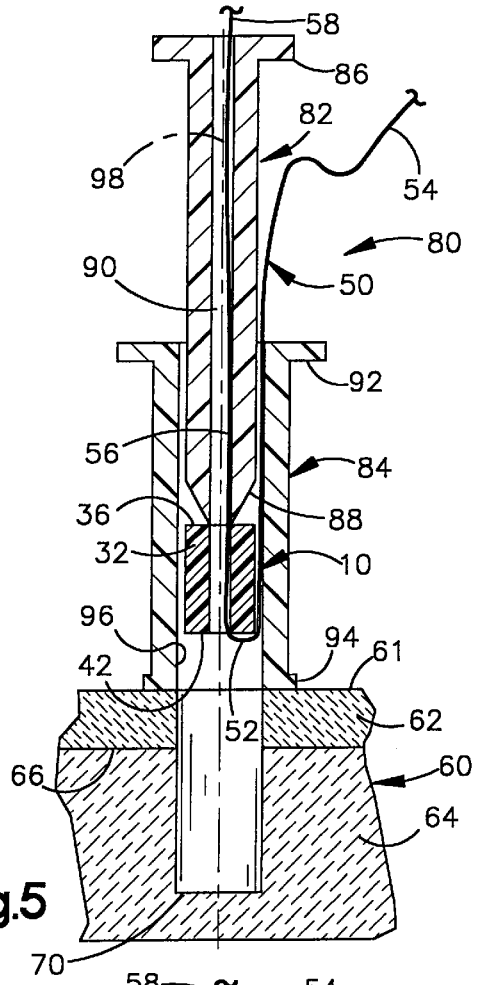
FIGS. 5–9 illustrate schematically the insertion of the suture anchor of FIG. 1 in bone with the aid of an inserter in accordance with the present invention.

The suture anchor 10 can be used to anchor the suture 50 in body tissue such as a piece of bone indicated schematically at 60 in FIG. 5. The bone 60 has an outer surface 61, a harder outer layer 62 of cortical bone and a softer inner layer 64 of cancellous bone or marrow. A more or less well defined boundary 66 separates the outer layer 62 from the inner layer 64.

An opening 70 is provided in the bone 60 to receive the anchor 10 to secure the suture 50 to the bone 60. The opening 70 may be a pre-existing opening or may be operatively provided as by drilling. The opening 70 preferably extends completely through the layer of cortical bone 62, as it is much more difficult to drive an anchor or suture through the hard cortical bone. It may be desirable to extend the opening 70 at least part way into the softer layer of bone 64, as illustrated in the drawings, to initially provide some room for the anchor 10 to change its orientation within the bone 60. It may not, however, be necessary to extend the opening 70 into the softer bone layer 64 as shown. The layer 64 may be soft enough to receive the anchor 10 directly.

The width of the opening 70 should be about the same size as or slightly larger than the width of the anchor 10. This will allow room for the anchor 10 to be satisfactorily driven into the bone 60, while minimizing the possibility of the anchor 10 accidentally backing out of the bone 60 through the opening 70. The opening 70 is preferably formed with a cannulated drill 99 (FIGS. 23–25) over the K-wire 98. The K-wire 98 is first inserted into the bone 60 (FIG. 23), through the cortical bone 62 into the cancellous bone 64. The cannulated drill 99 (FIG. 24) is then placed over the K-wire 98 and used to form the opening (FIG. 25) in the bone 60.

Figure 4:
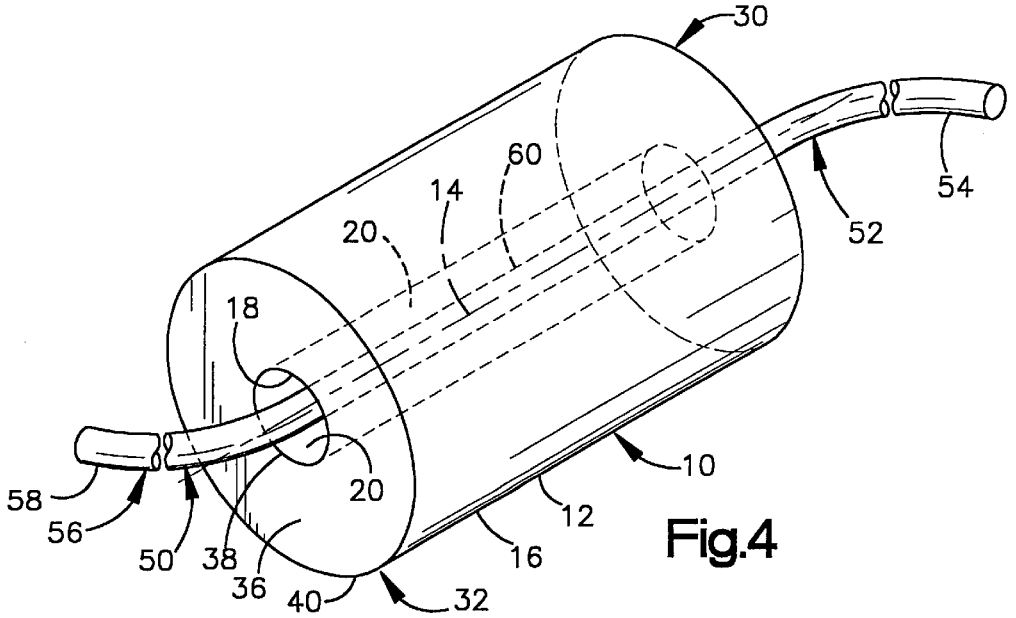
FIG. 4 is a perspective view showing a suture threaded through the suture anchor of FIG. 1.

After the suture 50 is threaded through the anchor 10 as illustrated in FIG. 4, the anchor is set in the bone 60 with the aid of an inserter 80 (FIG. 5.). The inserter 80 is a cannulated inserter (having the suture extending through it). The inserter 80 includes a pusher 82 and a guide 84. The pusher 82 is a cannulated or tubular member having a widened proximal end portion 86 and a tapering conical distal end portion 88. A central channel 90 extends through the length of the pusher 82. The pusher 82 is slidingly received in a central channel 96 of the tubular guide 84. The guide 84 has a widened proximal end portion 92 and a flanged distal end portion 94.

The inserter 80, the suture 50, and the anchor 10 are placed in the relative positions shown in FIG. 5 over a K-wire (indicated schematically at 98) extending through the central channel 90 of the pusher 82. The inserter guide flange portion 94 is placed against the outer surface 61 of the bone 60. The proximal end face 36 of the anchor 10 is in abutting engagement with the distal end portion 88 of the pusher 86. The proximal portion 56 of the suture 50 extends through the central channel 90 of the 92, and the proximal end 58 of the suture extends out of the inserter 80 to a location outside the bone 60. The distal portion 52 of the suture 50 wraps back around the anchor 10 proximally, and the distal end 54 of the suture extends out of the guide channel 96 to a location outside the bone 60.

The pusher 82 is then moved (FIG. 6) along the central channel 96 of the guide 84, toward the bone 60, until the anchor 10 is in the desired position in the opening 70 in the bone 60. The K-wire 98 is then removed to allow manipulation of the anchor 10.

Figure 6:
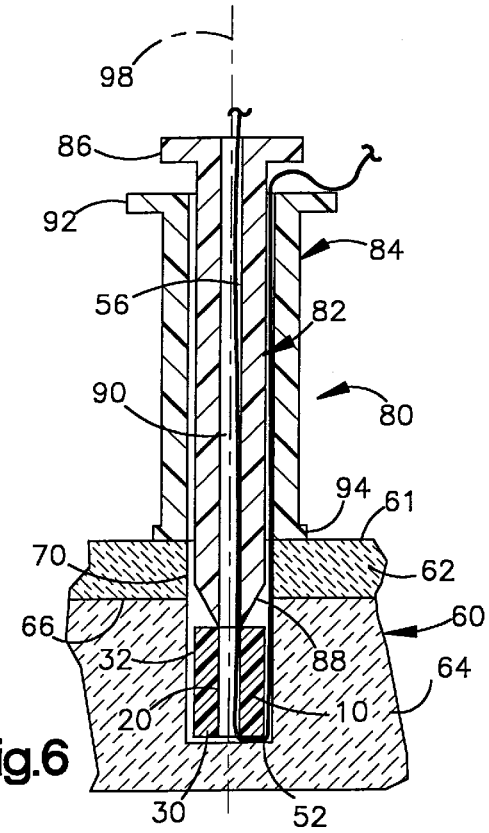

When the anchor 10 is in the insertion condition shown in FIG. 6, the intermediate portion 60 of the suture 50 is disposed within the anchor 10. The suture portion 52 extends distally out of the distal end portion 30 of the anchor 10. The suture portion 52 extends around the annular distal end face 42 of the anchor 10 and wraps back around the anchor 10 in a proximal direction. The suture portion 52 extends proximally along or past the outside of the anchor 10 to the proximal end portion 32 of the anchor 10 and thence proximally such that the distal end portion 54 of the suture 50 extends to a location outside the bone 60. Thus, when the anchor 10 is in position to be anchored in the bone 60, the suture 50 is threaded completely through the anchor 10 and both ends 54 and 58 of the suture project out of the opening 70 to a location outside of the bone 60.

Figure 7:
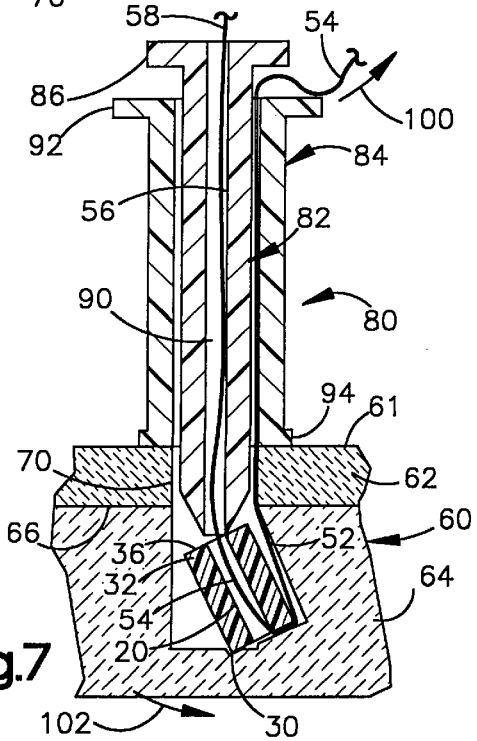
Figure 8:
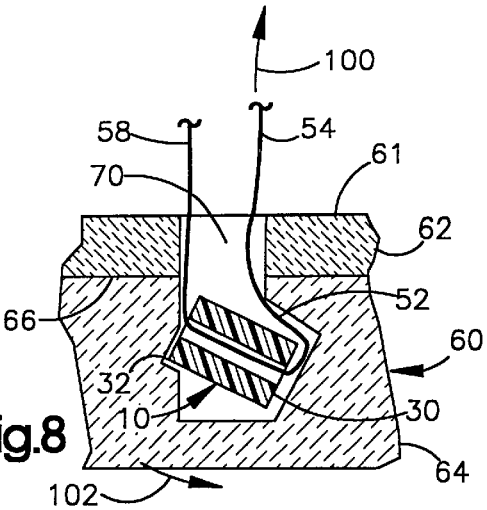
Figure 9:
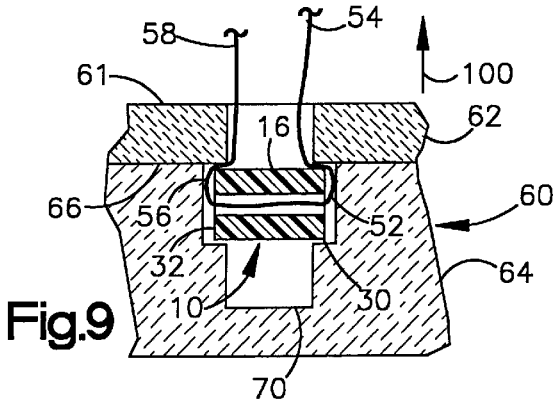

The orientation of the anchor 10 within the bone 60 is then changed to a blocking orientation as seen in FIGS. 7–9 to block removal of the anchor from the bone. The distal end 54 (FIG. 7) of the suture 50 is pulled proximally, as indicated by the arrow 100. This pulling force is transmitted through the suture portion 52 to the distal end portion 30 of the anchor 10. Because the suture portion 52 wraps around the distal end portion 30 of the anchor 10, tensile force on the suture portion 52 in the direction indicated by the arrow 100 imparts a pivoting or rotational moment to the anchor 10. The anchor 10 rotates or pivots in the direction indicated by the arrow 102 from the insertion condition shown in FIG. 6, through intermediate positions shown in FIGS. 7 and 8, to the blocking position or condition shown in FIG. 9. The tapered surface of the plunger end portion 88 aids in pivoting the anchor 10 as desired. The anchor 10 pivots relatively freely in the softer inner layer of bone 64.

To set the anchor firmly, both ends of the suture 50 are pulled outward to set the anchor 10 firmly against the outer layer of bone 62. In this position, the anchor 10 lies generally parallel to the surface of the bone 60 and generally perpendicular to the insertion direction of the opening 70. The distal suture portion 52 is clamped against the undersurface 66 of the cortical bone layer 62 by the outer surface 16 of the anchor 10 at the distal end portion 30 of the anchor. The proximal suture portion 56 is clamped against the undersurface 66 of the cortical bone layer 62 by the anchor outer surface 16 at the proximal end 32 of the anchor 10. Thus, the suture 50 is secured in the bone 60.

When the anchor 10 is in the blocking condition, the anchor is oriented in the bone 60 across the opening 70 in the outer bone layer 62. Because the anchor 10 is longer than it is wide, and because the opening 70 in the outer bone layer 62 is only large enough to accept the width of the anchor 10 and not the length of the anchor 10, the anchor cannot move through the opening in the outer bone layer when the anchor is in the blocking orientation or condition. The suture 50 may then be used to attach muscle or ligament or other tissue to the bone 60. The suture 50 may also be used to attach implants or other devices to the bone 60.

Figure 10A:
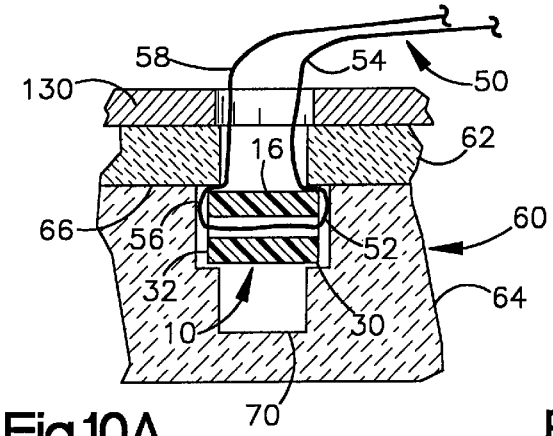
FIGS. 10A–10B illustrate schematically the use of the suture anchor for anchoring different objects to body tissue.
Figure 10B:
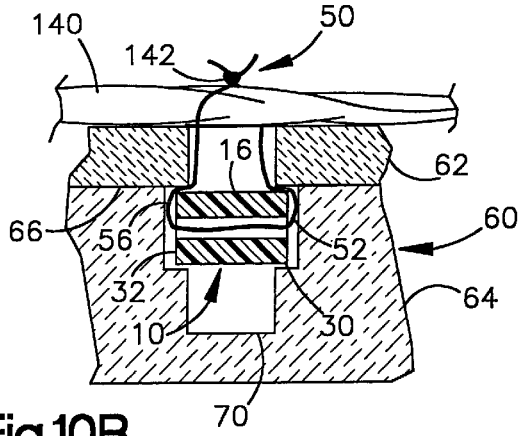

FIGS. 10A and 10B illustrate schematically several uses for the suture anchor 10. In FIG. 10A, the suture anchor 10 and the suture 50 are shown securing an implant or splint 130 to the bone 60. In FIG. 10B, the suture anchor 10 and the suture 50 are shown securing soft tissue such as a muscle 140 to the bone 60 with a knot 142. The suture anchor 10 can be used in any manner as needed for anchoring a suture to bone, soft tissue, etc.

Figure 23:
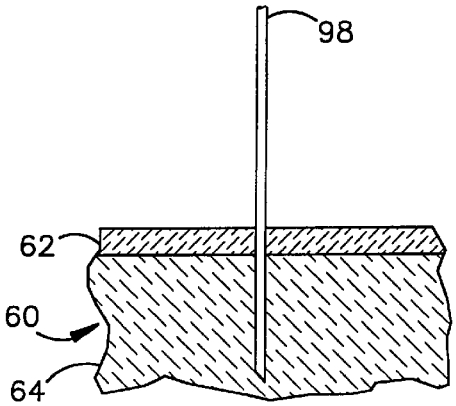
FIGS. 23–25 illustrate the forming of an anchoring opening in bone with a cannulated drill and a K-wire.
Figure 24:
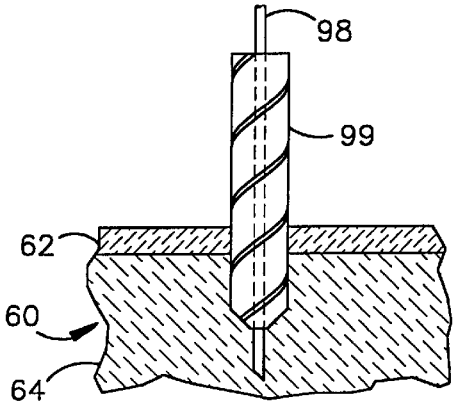
Figure 25:
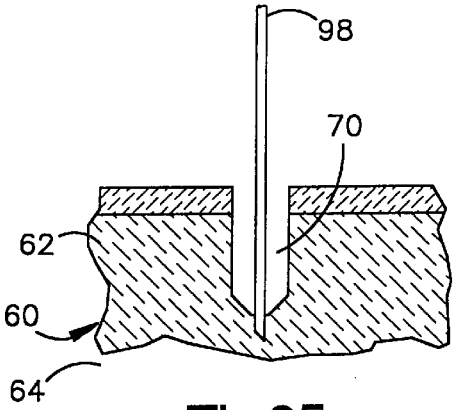

To aid in placement of the anchor 10 in the bone 50, a K-wire such as the K-wire 98 (FIGS. 5 and 6) is used. The K-wire is inserted into the bone 60 as shown in FIG. 23, preferably into the inner bone layer 64 past (deeper than) the point where the anchor will be. Next, a cannulated drill 99 (FIG. ) is placed over the K-wire 98 and rotated to make the opening 70 in the bone 60. FIG. 25 illustrates the opening 70 after drilling and removal of the drill 99. Note that the opening 70 is not as deep as the K-wire 98 is driven. The anchor is then inserted into the bone as discussed previously.

The suture anchor 10 is easily removable from the bone 60 without causing trauma to the bone. FIGS. 11–16 illustrate sequentially the removal process.

Figure 11:
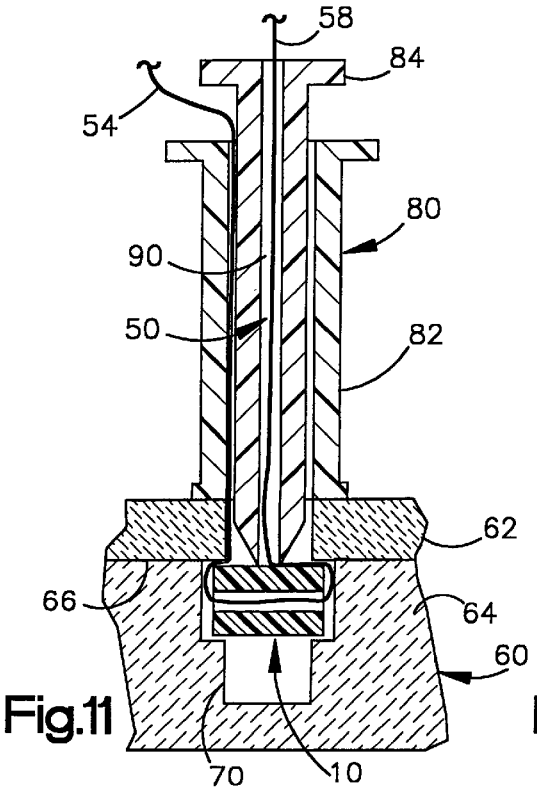
FIGS. 11–16 illustrate schematically the removal of the suture anchor.
Figure 12:
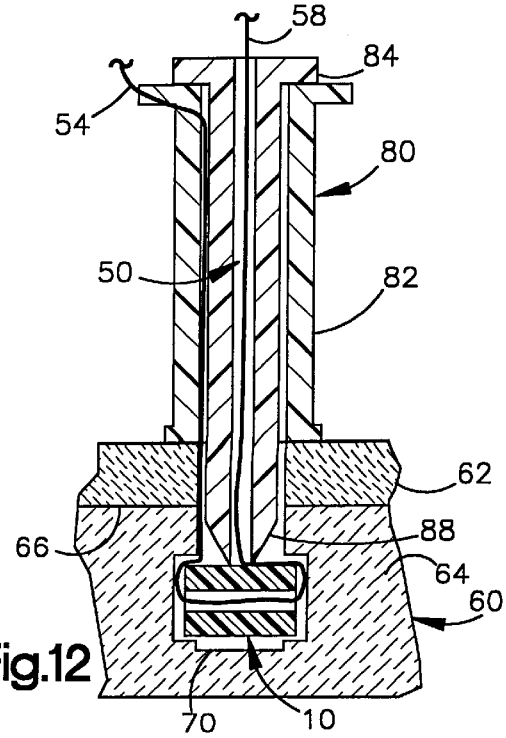
Figure 13:
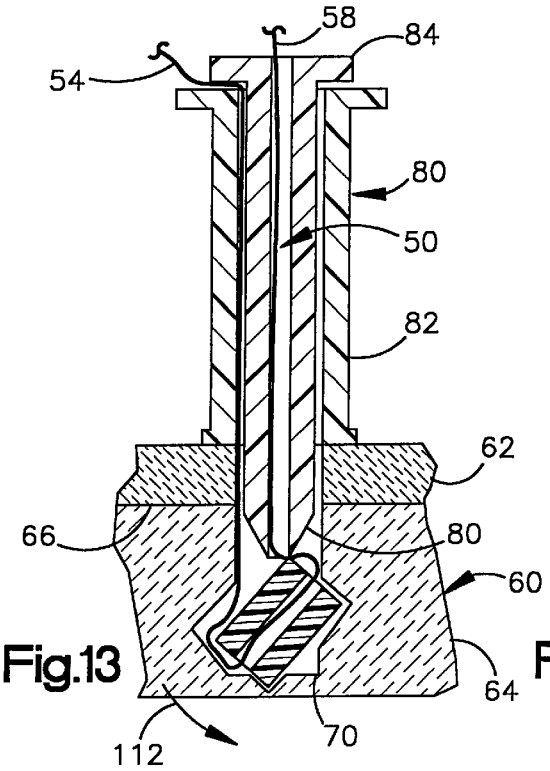
Figure 14:
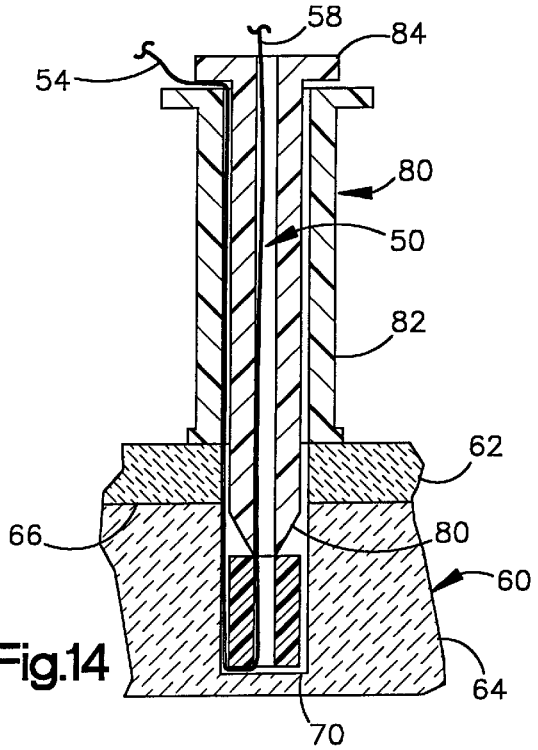

In FIG. 11, the anchor 10 is shown in its anchoring or blocking position lying parallel to the bone surface 61 and transverse to the opening 70. The inserter 80 is placed over the opening 70. One end 58 of the suture 50 is threaded up through the central opening 90 in the inserter pusher 84. The other end 54 of the suture 50 is threaded up between the pusher 84 and the guide 82 in the central channel 96 of the guide.

Figure 15:
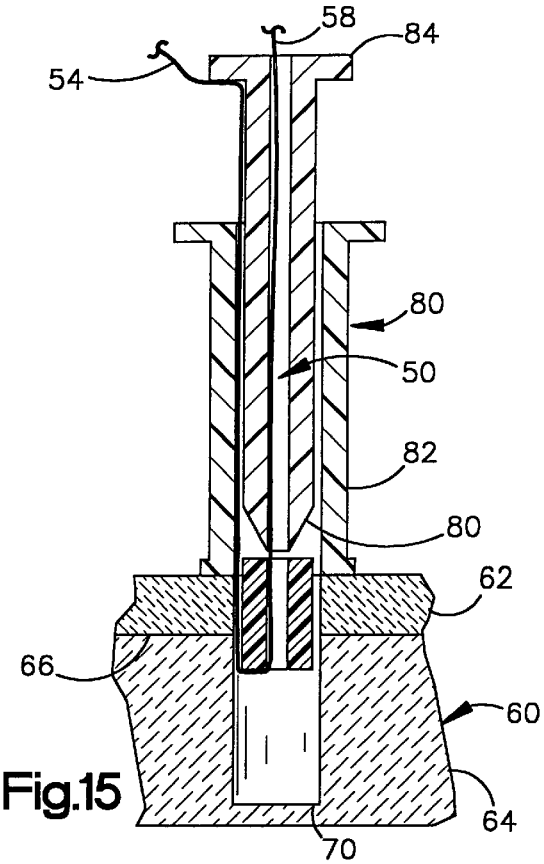
Figure 16:
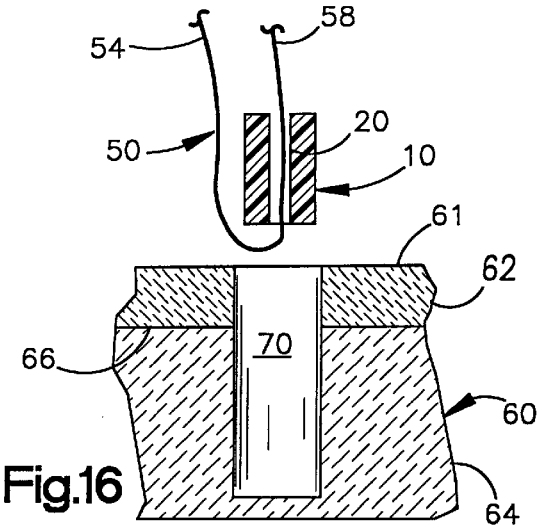
Figure 17:
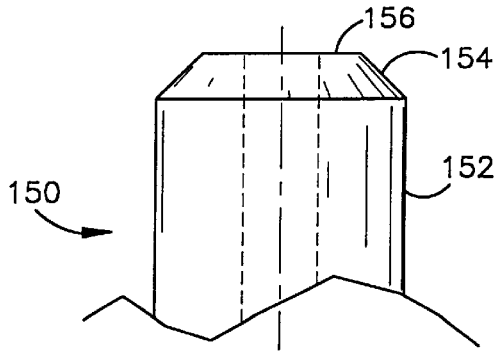
FIGS. 17–20 illustrate alternative anchor constructions.
Figure 18:
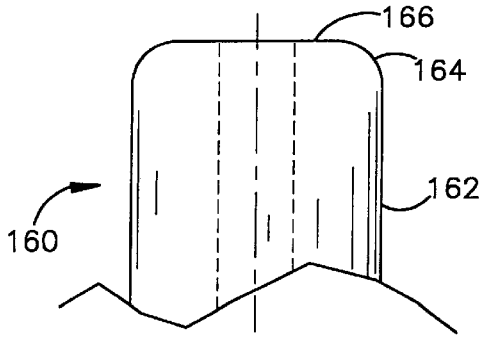
Figure 19:
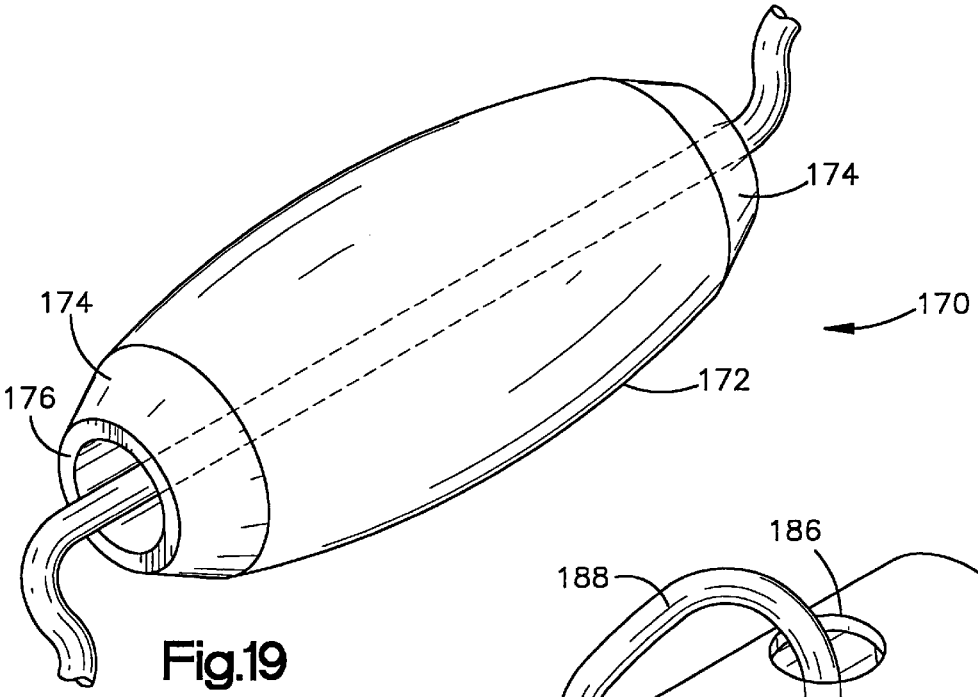
Figure 20:
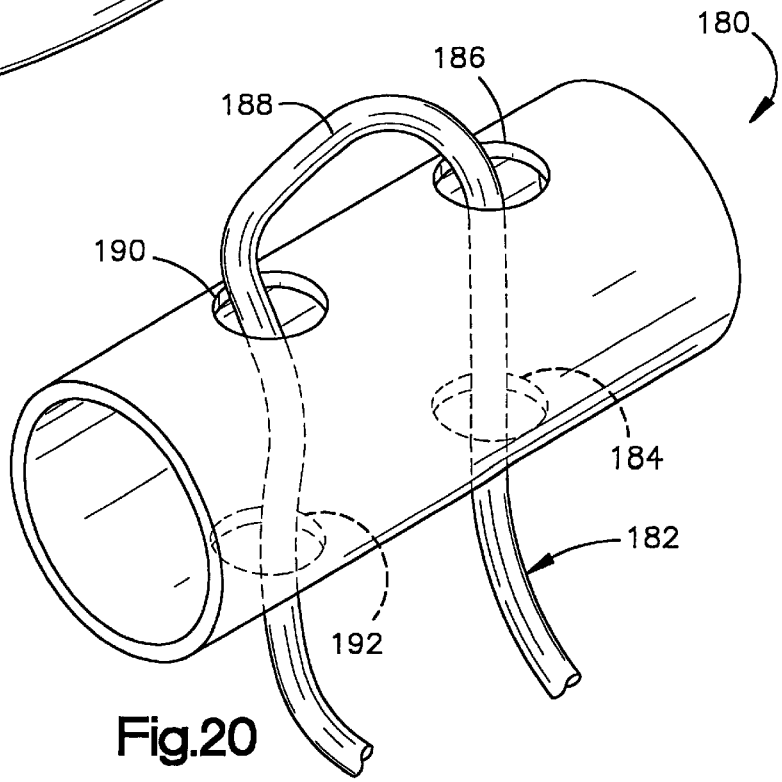

The pusher 84 is moved distally (down) into contact with the anchor 10 (FIG. 11). The pusher 84 (FIG. 12) is then moved further down into the bone 60 to move the anchor 10 away from the outer bone layer 62 and allow room for the anchor to rotate within the inner bone layer 64. The surgeon then pulls in the direction indicated by the arrow 110 (FIG. 13) on the suture end 58 which projects out of the central channel 90 of the pusher 84. The tensile force on the suture end 58 causes the anchor 10 to rotate within the bone 60 in the direction indicated by the arrow 112. The tapered pusher end portion 88 assists in initiating and controlling rotation of the anchor 10. The anchor 10 rotates within the bone 60 until it is disposed transverse to the bone surface 61 and parallel to the opening 70, as illustrated in Pig. 14. The anchor 10 is then in a release condition which is effectively the same as its insertion condition (FIG. 6). The anchor 10 and the pusher 84 are then removed distally from the bone 60 as illustrated in FIGS. 15 and 16.

This removal technique has been shown to work in 42 of 42 clinical trials.

There are several features of the anchors of the present invention which contribute to their ease of use, especially in removal. They do not anchor themselves by digging into tissue as does a screw or an anchor with a pointed end.

Instead, they rely on not being able to fit back through the hole they went in. Because they do not have axially inwardly extending slots or other non-uniform configurations at their ends, they can be turned within the cancellous bone to a vertical position (parallel to and aligned with the insertion opening) and thus made removable simply by pulling on the appropriate suture end. The non-oblique ends of the anchors, i.e., 90° end faces or curved or tapered end faces, do not bite into the bone and thus do not inhibit removability; rather, they allow easy rocking for change of orientation between insertion/removal and anchoring. The lack of knots avoids stress risers in the suture. There are no slots in the anchor to cut the suture.

FIGS. 17–20 illustrate schematically several alternative anchor configurations. An anchor 150 (FIG. 17) which is symmetrical end-to-end has a cylindrical outer surface 152 and two tapered end surfaces 154 (only one of which is shown). The tapered end surface 154 extends between an annular end face 156 and the cylindrical outer surface 152. An anchor 160 (FIG. 18) has a cylindrical outer surface 162 and a curved end surface 164. The curved end surface 164 extends between an annular end face 166 and the cylindrical outer surface 162. An anchor 170 (FIG. 19) has a cylindrical outer surface 172 and at each end a curved end surface 174. The curved end surfaces 174 extend between annular end faces 176 and the cylindrical outer surface 172. A tapered (non-90°) anchor end is not for the purpose of biting into the tissue to lock the anchor in place. It is for the purpose of the anchor pushing its way through intermediate tissue to get to the anchoring location. Then, the cocking (pivoting) of the anchor holds it in place. A sharp device can migrate within the body, which is highly undesirable.

An anchor 180 (FIG. 20) is similar to the anchor 10 (FIG. 1) but has four side openings through which a suture 82 enters and exits the anchor 180. The suture 182 extends into the anchor 180 through an opening 184 and passes out the opposite side through an opening 186. The suture 182 loops around at 188, extends back into the anchor 180 through an opening 190 and passes out the opposite side through an opening 192. With this anchor construction, also, pulling on one or the other of the projecting suture ends causes cocking or rotation of the anchor to change its orientation between an insertion or release condition to a blocking condition.

Figure 2:
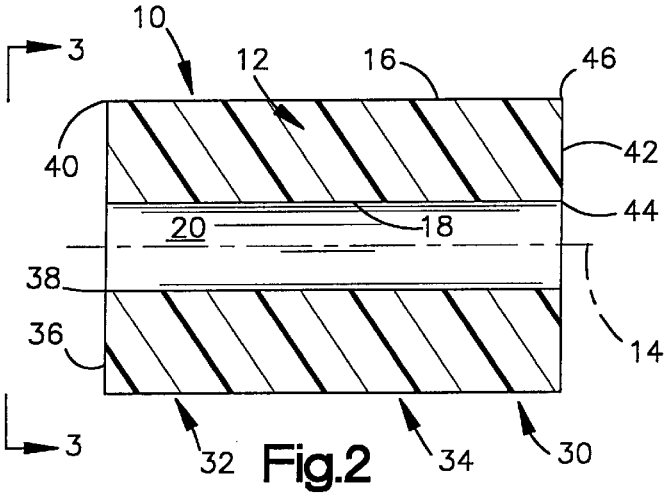
FIG. 2 is a longitudinal sectional view of the suture anchor of FIG. 1.
Figure 3:
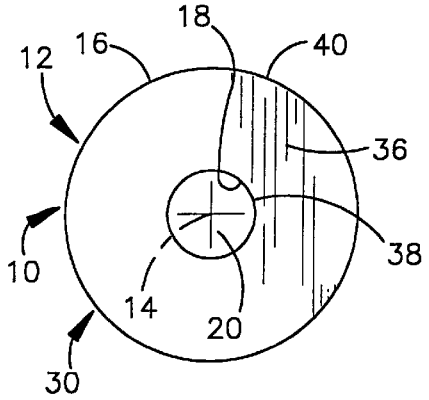
FIG. 3 is an end view of the suture anchor of FIG. 1 taken along line 3—3 of Pig. 2.

In the embodiments of FIGS. 1–17, 19 and 20, the anchors are uniform and have the same shape at each end. Thus, for example, the distance (i) from any first point on the end face 36 of the anchor 10 (FIG. 2) measured along a line extending parallel to the central axis 14 to a second point on the opposite end face 42, is the same as (ii) the distance from any third (other) point on the end face 36 measured along a line extending parallel to the central axis 14 to a fourth point on the opposite end face 42. Similarly, with the anchor 170 (FIG. 19), the distance (i) from any first point on one of the curved end surfaces 174 measured along a line extending parallel to the central axis of the anchor to a second point on the opposite curved end surface 174, is the same as (ii) the distance from any third (other) point on the first end surface 174 measured along a line extending parallel to the anchor central axis to a fourth point on the opposite curved end surface 174, is the third point is disposed on the anchor at the same distance from the axially outermost point of the first end of the anchor as is the first point.

Figure 22:
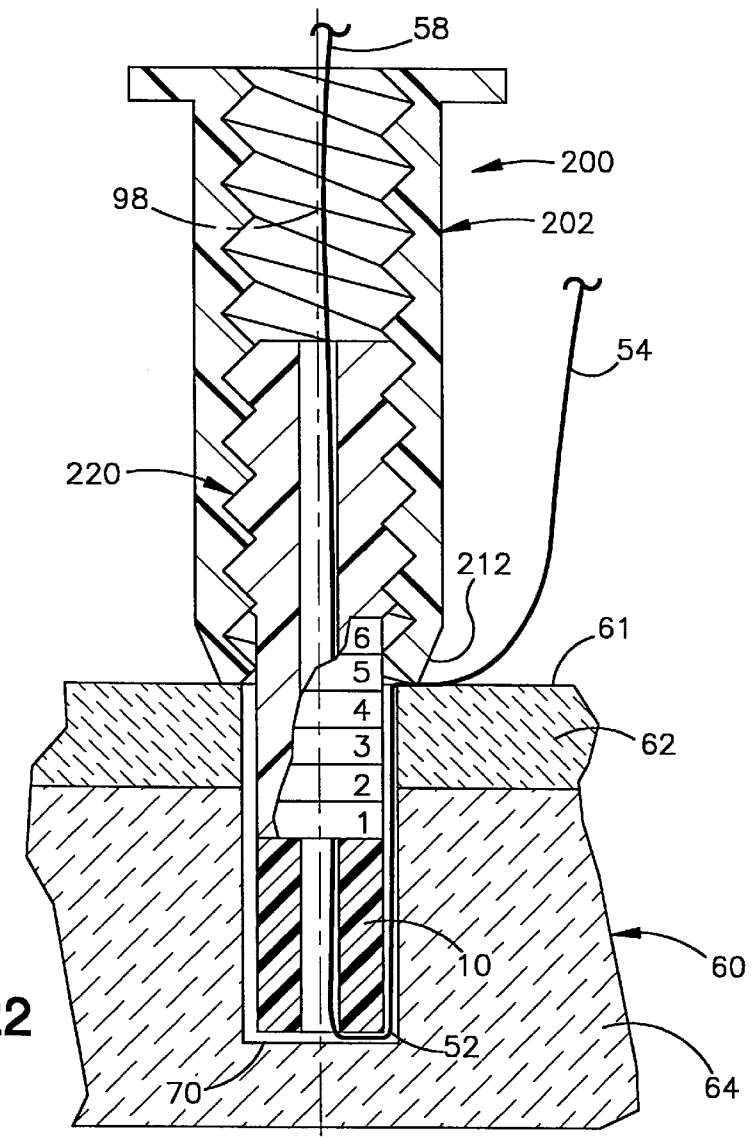
FIGS. 21 and 22 illustrate an alternative inserter constructions.
Figure 21:
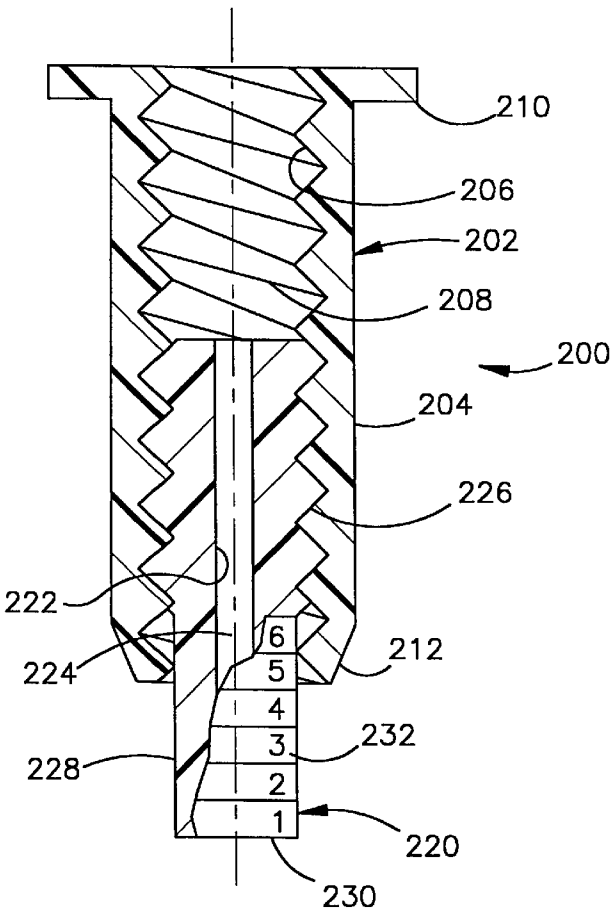

FIGS. 21 and 22 illustrate an alternative inserter construction. The inserter 200 (FIG. 21) includes a pusher 202 having a cylindrical wall 204. The wall 204 has a cylindrical inner surface 206 defining a central passage 208. The wall 204 has a handle 210 at its proximal end and a tapered distal end portion 212.

The inserter 200 includes a depth gauge 220 connected with the pusher 202 for movement with the pusher 202. The depth gauge 220 is a cylindrical member having an internal surface 222 defining a central passage 224 through the depth gauge. The depth gauge 220 has a threaded portion 226 threadedly received in the central passage 208 of the pusher 202. The depth gauge 220 has an indicator portion 228 projecting outwardly from the central passage 208 of the pusher 202. The indicator portion 228 has a distal end surface 230 and depth markings 232. The depth gauge 220 is rotatable within and relative to the pusher 202 to have a particular depth marking adjacent the distal end portion 212 of the pusher 202.

In use, the depth gauge 220 is set so that a particular depth marking is showing adjacent the distal end portion 212 of the pusher 202, corresponding to the estimated thickness of the cortical bone portion 62 at the location of anchor insertion. An anchor such as the anchor 10 is then placed on the distal end 230 of the depth gauge with a suture such as the suture 50 threaded through in the same manner as described above. The proximal end 58 of the suture 50 extends through the central passage 224 of the depth gauge 220 and through the central passage 208 of the pusher 202 to a location outside the body. The distal end 54 of the suture 50 extends through the opening 70 around the outside of the depth gauge indicator portion 228 and past the tapered end portion 212 of the pusher 202 to a location outside the body.

The assembly is moved into the opening 70 as shown in FIG. 22, possibly over a K-wire 98. When the distal end portion 212 of the pusher 202 engages the outer surface 61 of the bone 60, the anchor 10 is in its proper position. The inserter 200 and the K-wire 98 may then be removed. The anchor 10 is then rotated within the softer inner layer 64 of the bone 60 to an anchoring position as shown in FIG. 9.

The methods and principles involved in soft tissue anchoring are similar to those involved in anchoring in bone. In joining soft tissue to soft tissue, it is preferable to insert the anchor directly through the soft tissue, not into an opening in the tissue. Thus, the anchor may have a slightly sharpened or pointed distal end (tip) to push through the tissue layers. Also, both the anchor and the insertion tool may be made curved, or may be made of an elastic material, in order to be able to be pushed over a curved K-wire.

In bone it is necessary to drill a hole to get the anchor into position. Unlike bone, soft tissue is highly visco-elastic. In soft tissue, one can simply push the tissue away from the intended location of the anchor. As the anchor is pushed through a certain location by the insertion tool, the tissue is pushed from that location. Once the anchor is pushed through a position by the insertion tool, the tissue pushed away will collapse back over the suture and not allow the anchor to be pulled out easily.

In soft tissue applications, the needle goes in to the tissue first. It can be straight or curved. The curved needle may be enough to cut the way into the soft tissue, like a knife cutting a slot for a meat thermometer in a roast. A tapered or bullet shaped anchor pushes the tissue out of its way as it proceeds along the needle/guide wire.

Figure 26:
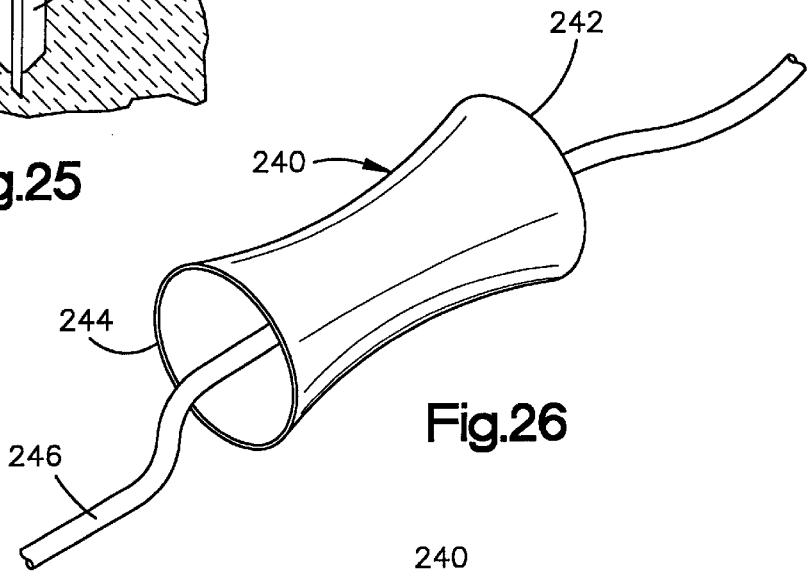
FIG. 26 is a pictorial view of an alternative anchor construction.
Figure 27:
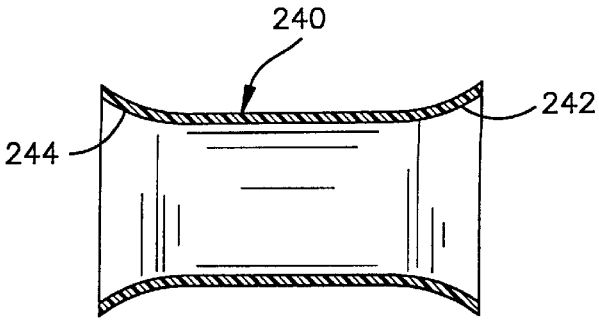
FIG. 27 is a longitudinal sectional view of the anchor of FIG. 26.

FIGS. 26 and 27 illustrate an alternate anchor construction. The anchor 240 is of a generally cylindrical construction like the anchor 10. The anchor 240 has end portions 242 and 244 which flare radially outwardly. This can minimize cutting of a suture passing through the anchor 240, such as the suture 246. In any of these anchor constructions, it is desirable to avoid sharp edges, and so the ends may be rounded or polished or de-burred.

From the above description of the invention, those skilled in the art will perceive improvements, changes and modifications in the invention. Such improvements, changes and modifications within the skill of the art are intended to be covered by the appended claims.

I claim:

1. An apparatus comprising a suture anchor inserter, said suture anchor inserter including an outer tube and an inner tube, said inner tube being at least partially disposed in said outer tube and being slidable relative to said outer tube, said inner tube having surface means for defining a central channel, a thin elongated member at least partially disposed in said central channel, said thin elongated member having an end portion adapted to be disposed in engagement with body tissue, a suture at least partially disposed in said central channel, and an anchor, said anchor having surface means for defining a passage through which said thin elongated member and said suture extend, said anchor being movable along said thin elongated member from a first position in which said anchor is at least partially disposed within said outer tube to a second position in which said anchor is outside of said outer tube and is disposed in engagement with body tissue, said suture and said thin elongated member being disposed in said passage in said anchor throughout movement of said anchor from the first position to the second position.

2. An apparatus as set forth in claim 1 wherein said inner tube has surface means for applying force against said anchor to move said anchor from the first position to the second position.

3. An apparatus as set forth in claim 2 wherein said outer tube includes surface means for engaging the body tissue to retain said outer tube against movement relative to the body tissue during movement of said anchor from the first position to the second position.

4. An apparatus as set forth in claim 2 wherein said outer tube has inner side surface means for defining a channel in which said inner tube is received, said inner tube having outer side surface means for engaging said inner side surface means on said outer tube to guide movement of said inner tube relative to said outer tube, a portion of said suture being disposed between said inner side surface means on said outer tube and said outer side surface means on said inner tube during movement of said anchor from the first position to the second position.

*5. An apparatus which is adapted to be at least partially received in body tissue, said apparatus comprising an anchor having a cylindrical outer side surface with a longitudinal central axis, said anchor including first surface means for at least partially defining a first passage which extends through said anchor at a location disposed between and spaced from axially opposite ends of said anchor, said first passage extends through said longitudinal central axis of said anchor, said anchor including second surface means for at least partially defining a second passage which extends through said anchor at a location spaced from said first passage and disposed between and spaced from axially opposite ends of said anchor, said second passage extends through said longitudinal central axis of said anchor at a location which is spaced from said first passage, said anchor including third surface means for defining a third passage which extends along said longitudinal central axis of said anchor and intersects said first and second passages, and suture means for extending into body tissue, said suture means having a first portion which extends through said first passage in said anchor, a second portion which extends along said cylindrical side surface of said anchor between ends of said first and second passages, and a third portion which extends through said second passage in said anchor.*

*6. An apparatus which is adapted to be at least partially received in body tissue, said apparatus comprising an anchor having a cylindrical outer side surface with a longitudinal central axis, said anchor including first surface means for at least partially defining a first passage which extends through said anchor at a location disposed between and spaced from first and second axial ends of said anchor, said first passage extends through said longitudinal central axis of said anchor, said anchor including second surface means for at least partially defining a second passage which extends through said anchor at a location spaced from said first passage and disposed between and spaced from said first and second axial ends of said anchor, said second passage extends through said longitudinal central axis of said anchor at a location which is spaced from said first passage, said anchor including third surface means disposed on said first axial end of said anchor for receiving force to press said second axial end of said anchor against body tissue and to urge said anchor to rotate about an axis which extends transverse to the longitudinal central axis of said anchor while said anchor is at least partially enclosed by body tissue, and suture means for extending into body tissue and for transmitting force to said anchor to urge said anchor to rotate about the axis which extends transverse to the longitudinal central axis of said anchor while said anchor is at least partially enclosed by body tissue, said suture means having a first portion which extends through said first passage in said anchor, a second portion which extends along said cylindrical side surface of said anchor between ends of said first and second passages, and a third portion which extends through said second passage in said anchor.*

* * * * *